United States Patent [19]

Heimburger et al.

[11] Patent Number: 5,424,401
[45] Date of Patent: Jun. 13, 1995

[54] PROCESS FOR THE PREPARATION OF A STABLE FACTOR VIII

[75] Inventors: Norbert Heimburger; Klaus Wellner, both of Marburg; Karl-Heinz Wenz, Argenstein; Gerhardt Kumpe, Wetter, all of Germany

[73] Assignee: Behringwerke Aktiengeseschaft, Marburg, Germany

[21] Appl. No.: 166,156

[22] Filed: Dec. 14, 1993

Related U.S. Application Data

[63] Continuation of Ser. No. 953,204, Sep. 29, 1992, abandoned, which is a continuation of Ser. No. 562,570, Aug. 3, 1990, abandoned.

[30] Foreign Application Priority Data

Aug. 7, 1989 [DE] Germany .................. 39 26 034.8

[51] Int. Cl.$^6$ .................. C07K 1/18; C07K 14/755
[52] U.S. Cl. .................. 530/383; 530/381; 530/415; 530/416
[58] Field of Search .................. 530/381, 383, 415, 416

[56] References Cited

U.S. PATENT DOCUMENTS

| | | | |
|---|---|---|---|
| 4,093,608 | 6/1978 | Iga et al. | 530/383 |
| 4,272,523 | 6/1981 | Kotitschke et al. | 530/383 |
| 4,297,344 | 10/1981 | Schwinn et al. | 530/381 |
| 4,305,870 | 12/1981 | Liu et al. | 530/381 |
| 4,743,680 | 5/1988 | Matthews et al. | 530/383 |
| 5,252,709 | 10/1993 | Burnouf et al. | 530/381 |
| 5,371,195 | 12/1994 | Grandgeorge et al. | 530/383 |

FOREIGN PATENT DOCUMENTS

| | | | |
|---|---|---|---|
| 1265051 | 1/1990 | Canada . | |
| 0018561 | 11/1980 | European Pat. Off. . | |
| 0083483 | 7/1983 | European Pat. Off. . | |
| 0173242 | 3/1986 | European Pat. Off. . | |
| 0245875 | 11/1987 | European Pat. Off. | 530/383 |
| 2636757 | 2/1987 | Germany | 530/383 |

OTHER PUBLICATIONS

Fay et al., "Purification And Characterization of a Highly Purified Human Factor VIII consisting of a Single Type of Polypeptide Chain," Proc. Nat'l. Acad. Sci, USA, vol. 79, pp. 7200–7204, Dec. 1982.

S. van Creveld et al., "The Separation of AHF from Fibrinogen," Thromb. Diathes, VI(2/3), pp. 282–286, 1961.

Baugh et al., "Separation of Human Factor VIII Activity from the Von Willebrand's Antigen and Ristocetin Platelet Aggregating Activity," Biochimica et Biophysica Acta, vol. 371, pp. 360–367, 1974.

*Primary Examiner*—Jeffrey E. Russel
*Attorney, Agent, or Firm*—Finnegan, Henderson, Farabow, Garrett & Dunner

[57] ABSTRACT

A process for the preparation of a pasteurized factor VIII concentrate with high specific activity and stability is described, which comprises adsorbing impurities from the solution containing the factor VIII by at least two-fold adsorption with $Al(OH)_3$, an anion exchanger or $Ca_3(PO_4)_2$, preferably with two different adsorbents from this group.

16 Claims, No Drawings

PROCESS FOR THE PREPARATION OF A STABLE FACTOR VIII

This application is a continuation of application Ser. No. 07/953,204, filed Sep. 29, 1992, now abandoned, which is a continuation of application Ser. No. 07/562,570, filed Aug. 3, 1990, abandoned.

The invention relates to a process for the preparation of a pasteurized factor VIII concentrate with high specific activity and stability, which comprises adsorbing impurities from a solution containing the factor VIII by at least two-fold adsorption with $Al(OH)_3$, an anion exchanger or $Ca_3(PO_4)_2$, preferably with two different adsorbents from this group.

The clotting of plasma is an enzymatic process; the factors involved in it are proteins, having the property of proteases in most cases, which proteins circulate in the blood in the form of their inactive precursors and are only activated on contact with wettable surfaces or else in cases of injury. In addition to thrombin, other clotting proteases, e.g. factors Xa and IXa, also attack factor VIII and are able to inactivate it. Protein C which is also able to inactivate factor Va is also of particular importance. Factors V and VIII are the most labile clotting factors. They start to decompose from the instant blood is removed. An additional contributor to this is that they are stabilized by $Ca^{2+}$ and the removal of blood is carried out with complexing agents such as citrate and EDTA. These known data are in accordance with the observation that only 40 to 60% of the factor VIII activity from human plasma can still be found in the cryoprecipitate from human plasma which, throughout the world, is used as starting material for obtaining factor VIII, and that only 10 to 20% thereof still remains after the purification of factor VIII. This is a severe handicap to supplying hemophiliacs; on the one hand, blood as a raw material is not only precious and of only very limited availability but, on the other hand, the low yields affect the price. This has been most particularly true since the introduction of additional stages of processing which guarantee the inactivation of viruses in the production of factor VIII.

For factor VIII prepared by conventional methods, Fay et al. (Proc. Natl. Acad. Sci., USA, 79,7200, 1982) report a yield of 12.7%. Zimmerman and Fulcher achieve an almost identical value using modern immunoaffinity chromatography methods (EP-A-0,083,483).

Many authors have described that factor VIII binds strongly to DEAE exchangers and ECTEOLA but that although it is possible to displace it again using halides it loses its activity within 24 hours (S. van Creveld et al., Thromb. Diathes. VI (2/3), 282, 1961; R. Baugh et al., Biochim. Biophys. Acta 371, 360, 1974), but no solution to this problem has been offered since additions of proteinase inhibitors such as PMSF (phenylmethanesulfonyl fluoride) and benzamidine are not suitable for producing a human preparation.

As a result of the situation which has been described, there was an urgent need for measures which prevent decomposition of factor VIII during processing and purification and can be used as early as possible, i.e. right at the start of the isolation or the purification. Chosen as an early point in time was the further processing of cryoprecipitate which, starting from plasma, is obtained by so-called cryoprecipitation and is also marketed as a raw material.

The dissolved cryoprecipitates are, according to the state of the art, as a rule treated with $Al(OH)_3$ in order to eliminate traces of contamination with prothrombin factors (factor II, VII, IX, X). This is intended to prevent activation of these factors which might degrade factor VIII during the purification. Surprisingly, we have found that a single adsorption of a fresh solution of cryoprecipitate with $Al(OH)_3$ is not sufficient to remove the prothrombin factors and other proteases, since even after the adsorption a distinct amidolytic activity could be detected in the supernatant of the adsorbed solution, with the F Xa test having the highest sensitivity, although this activity does not seem to be identical to F Xa.

Surprisingly it has been found that a stable factor VIII which is easy to handle with low losses can be obtained by pretreating a cryoprecipitate, for example by multiple adsorption on $Al(OH)_3$, $Ca_3(PO_4)_2$ or anion exchanger or also mixed adsorptions. As criterion therefor, the amidolytic activity, the yield, the specific activity and the stability at room temperature of the final product are determined.

The invention therefore relates to measures which, when applied to a freshly dissolved cryoprecipitate, prevent loss of a large proportion of the factor VIII activity during the purification and pasteurization and which lead to a final product which has a high specific activity, nativeness and stability in a good yield.

The invention particularly relates to a process for treating F VIII-containing plasma fractions such as those which are customarily used for the preparation of F VIII, preferably for treating dissolved cryoprecipitate or Cohn fraction I, which process comprises treating these with adsorbents which bind enzymes and proenzymes which have amidolytic/proteolytic activity and degrade F VIII, after which a stable and, if appropriate, pasteurized factor VIII can be obtained in good yield by methods known per se.

The invention particularly relates to a process for the preparation of factor VIII with high specific activity and stability, which comprises subjecting a factor VIII-containing solution, such as one of cryoprecipitate, to at least two adsorptions on $Al(OH)_3$, an anion exchanger or $Ca_3(PO_4)_2$ before obtaining factor VIII by methods known per se from the solution which has been pretreated in this way.

Such known methods are, for example, described in EP-A-0,018,561 or EP-A-0,173,242.

The F VIII-containing starting material is preferably adsorbed with a mixture of at least two different adsorbents. It is advantageous to carry out a treatment with $Ca_3(PO_4)_2$ or else with a basic anion exchanger having a hydrophilic matrix, for example based on polysaccharides such as cellulose or crosslinked polysaccharides, and functional groups such as those which are for example characteristic of DEAE-$^R$Sephadex, ECTEOLA or QAE-$^R$Sephadex (QAE).

The type and amount of adsorbent (as a rule 1–3% W/V) are selected with a view to the adsorption and removal of zymogens and enzymes, mainly proteinases, which can be present in association with F VIII, but not of F VIII. The amidolytic activity of the final product is determined as an indicator of this, preferably using chromogenic peptides such as those which are employed in the determination of F Xa and which are commercially available. The F VIII final product should be virtually free thereof.

When several adsorbents are used, individual addition and separation off thereof is possible, but they are preferably added sequentially at intervals of from 1 min to 30 min and separated off together. A preferred embodiment provides for removal by centrifugation of all the added adsorbents after adsorption times of 1–30 min.

A cryoprecipitate solution (cryosolution) may advantageously be treated at a pH of 6.5–7.5 and physiological ionic strength (10–15 mS), preferably in a medium which does not contain any citrate ions or other traps for divalent metal ions, at best initially with Al(OH)$_3$, but also together with Ca$_3$(PO$_4$)$_2$ and/or DEAE exchanger and/or ECTEOLA and/or QAE. For the treatment to be effective it is necessary to add the adsorbents in a chronological sequence. The separation off by centrifugation may be carried out in one step.

The results of such adsorptions, mainly with mixtures of adsorbents, are listed in Table 1. They can be summarized as follows:

The amidolytic activity which still remains in the cryosolution even after the second Al(OH)$_3$ adsorption and can be detected in the final product can be reduced drastically only by a further subsequent adsorption with Ca$_3$(PO$_4$)$_2$ and/or ECTEOLA and/or QAE or another basic ion exchanger; a mixture of several ion exchangers is also effective.

Surprisingly, the treatment does not result in any loss of factor VIII activity when a specific amount of adsorbent is not exceeded. This is 10 g of moistened exchanger per liter of cryosolution for Ca$_3$(PO$_4$)$_2$ and about 20 to 30 g for QAE and ECTEOLA. Such a solution is customarily obtained by dissolving 1 kg of cryoprecipitate in 3 l of buffer solution.

$^R$Sephadex and a mixture of these anion exchangers in combination with a preceding Al(OH)$_3$ absorption. The result of the mixed adsorption with QAE-$^R$Sephadex and Ca$_3$(PO$_r$)$_2$ is noteworthy because, with a high yield, it leads to a product of good specific activity and sufficient stability; dialysis for 20 hours at 20° C. and storage for 24 hours at 20° C. represent severe stresses and the loss of activity was only a total of 11%. It remains to be noted that such stable and, at the same time, such low-protein F VIII solutions with specific activities of about 100 U/mg had not been described hitherto. The storage for 4 days at room temperature has to be regarded as a stress test in order to detect even the slightest traces of enzymatic impurities which destroy factor VIII.

It can be stated that the loss of F VIII activity during storage is attributable to contamination of the F VIII concentrates with proteases and that this correlates with the residual amidolytic activity in the final product (see Table 1).

A sample which has been adsorbed once with Al(OH)$_3$ contains cleavage products corresponding to a molecular weight of 50 to 40 kDa even after dialysis and it decomposes virtually completely into even smaller subunits (smaller than 40 kDa) during storage. In contrast, the sample which has been treated twice with Al(OH)$_3$ plus QAE and ECTEOLA is stable for 48 hours. This is in good agreement with the F VIII activities measured during storage and is attributable to the low amidolytic activity of this sample.

The invention relates to a highly purified factor VIII concentrate with good clinical recovery and half-life and to a process for its preparation and pasteurization with good yield and stability, which comprises treating

TABLE 1

Pretreatment of a solution of cryoprecipitate with adsorbents and basic ion exchangers: influence on yield, specific activity and stability of F VIII which has been prepared according to EP-A 0,173,242 or DE 3,432,083 A1

| Experiment No. | Pretreatment with adsorbents | Amidolytic activity* $\Delta OD_{405}$ nm/min × 10$^{-3}$ | Spec. activity* (IU/mg) | Process yield (%)* | Loss of F VIII activity during dialysis (20 h) (%) | Loss of F VIII activity during storage at room temperature (20° C.) reported in F VIII activity after dialysis (= 100%) | | |
|---|---|---|---|---|---|---|---|---|
| | | | | | | 24 h | 48 h | 96 h |
| 1 | Al(OH)$_3$,1× | 31.5 | 56 | 48 | 19 | 29 | 70 | 98 |
| 2 | Al(OH)$_3$,2× | 22.0 | 75 | 44 | 5 | 12 | 23 | 37 |
| 3 | Al(OH)$_3$,2× ECTEOLA | 3.65 | 159 | 54 | 0.3 | 4 | 9 | 24 |
| 4 | Al(OH)$_3$,2× QAE | 1.85 | 144 | 54 | 8 | 5 | 7 | 23 |
| 5 | Al(OH)$_3$,2× QAE,ECTEOLA | 0.87 | 215 | 53 | 0 | 0 | 3 | 19 |
| 6 | Al(OH)$_3$,2× QAE, Ca$_3$(PO$_4$)$_2$ | 7.27 | 184 | 55 | 1 | 10 | 36 | 63 |

*determined on the final product
1 = state of the art

By pretreating the cryosolution with adsorbents and anion exchangers, unspecific proteins are also removed in addition to the amidolytic activity. As a result both the factor VIII yield and the specific activity are increased. The pretreatment of the fresh cryosolution with adsorbents and ion exchangers furthermore has the advantage that it leads to a stable intermediate product which can be pasteurized at 60° C. in aqueous solution almost without any loss and is easier to handle. It leads to a stable final product which can be dialyzed, filtered and stored without great losses of activity.

The most effective pretreatment of the cryosolution was that with ECTEOLA, QAE-$^R$Sephadex, DEAEthe raw material, especially cryoprecipitate, after dissolving with adsorbents such as Al(OH)$_3$, Ca$_3$(PO$_4$)$_2$ and basic ion exchangers (DEAE, QAE, ECTEOLA) until the solution is free of amidolytic activity, as determined on the final product.

It is possible to carry out this determination with the substrate S-2222 from Kabi (Bz-Ile-Glu-Gly-Arg-pNA) in the way in which it is used for the determination of factor X; BCP 200, Z-D-Leu-Gly-Arg-MNA from Behringwerke AG or $^R$Chromozym TH from Boehringer Mannheim GmbH are likewise suitable.

Determination of factor VIII

The determination of factor VIII is, for example, carried out by the following process:

1 part, e.g. 0.1 ml of partial thromboplastin, e.g. prepared according to Patent Application P 23 16 430.9-52 (Ma 160) is mixed with one part of factor VIII-deficient plasma and one part of dilute normal plasma. This mixture is kept at 37° C. for 6 min. After the addition of one part of a 0.025 molar calcium chloride solution which has been preheated to 37° C., the time which elapses from the addition of the calcium chloride solution until clotting occurs is determined. For quantitative evaluation the clotting time resulting from the factor VIII-containing solution is used to read off a calibration plot obtained by serial dilution of normal plasma. 1 international unit (=1 IU) of factor VIII corresponds to the factor VIII activity of 1 ml of normal plasma.

Determination of the amidolytic activity

This can, for example, be carried out according to the principle of a factor Xa determination.

Determination mixture

100 μl of sample+500 μl of buffer solution, 50 mmol/l Tris, 150 mmol/l NaCl, pH 8.2,+100 μl of substrate, BCP 200, 3 mmol/l, or S-3333, 3 mmol/l Preincubate at 37° C. for 5 minutes and then measure the conversion of substrate for 20 minutes at 37° C. and 405 nm; evaluate the amidolytic activity in delta OD/min.

Measures for stabilizing factor VIII can be used for all preparation processes which have been described hitherto in a fashion substantially independent of the starting material, e.g. according to DE 3,432,083 or EP 0,018,561, or DE 3,432,083 or EP 0,173,242 as is proved below by examples. The buffers used below are described after the examples.

EXAMPLE 1

Starting material 1 kg of cryoprecipitate was dissolved at +37° C. in 3 l of dissolving buffer and then treated with 1×8% (v/v) Al(OH)$_3$ 4 l of solution were adsorbed at +25° C. for 15 minutes with 320 ml of 1% strength Al(OH)$_3$. The adsorbent was centrifuged off at 3,000 rpm for 15 min and stabilizers were added to the supernatant of the adsorbed cryosolution.

Stabilizing and heating

For this purpose, if the 4,040 ml of the Al(OH)$_3$ supernatant were made up to a final concentration corresponding to 100% (w/v) by the addition of 4,040 g of sucrose; subsequently, 545.4 g of glycine corresponding to 1.8 mol/l were added and the CaCl$_2$ concentration was adjusted to 5 mmol/l. The stabilized solution was adjusted to pH 7.3 with 2.5N NaOH and was then heated at +60° C. for 10 hours. The F VIII:C activity was determined before and after heating and was 2.0 U/ml and 1.6 U/ml, respectively.

Preparing for the DEAE adsorption according to DE 3,432,083

The heated cryosolution (6,868 ml) was diluted with 6,868 ml of dilution buffer and the pH was adjusted to 5.5 with 2N acetic acid.

Adsorption on DEAE-$^R$Sepharose CL-6B in batch process 13,736 ml of dilute pasteurized cryosolution were adsorbed at room temperature for 4 hours with 300 ml of equilibrated DEAE-$^R$Sepharose CL-6B, and the Sepharose was then separated off.

Washing the $^R$Sepharose and transferring it into a column

The Sepharose loaded with F VIII was prewashed on a suction filter, then transferred into a column (diameter 7.2 cm) and treated with 3 l of washing buffer.

Elution of the DEAE-$^R$Sepharose column

The F VIII:C was displaced from the washed DEAE-$^R$Sepharose with an acetate-buffered and lysine-containing CaCl$_2$ solution (0.3 mol/l), and the eluate, 195 ml, was made up to a final concentration of 0.75% by the addition of 1.46 g of sucrose.

Dialysis 195 ml of eluate were dialyzed at +4° C. for 16 hours against 20 l of dialysis buffer. Of this material, the protein content was measured (OD$_{280nm}^{1\%}$=10 mg/ml), the F VIII activity was determined and the yield and specific activity was calculated from the two values; in a stress test, portions were stored at 20° C., and the F VIII activity was determined after 24, 48 and 96 hours (see table, Experiment 1).

Adjusting the concentration and sterilization by filtration 218 ml of dialyzed F VIII:C were rendered sterile by filtration through Sartorius filters; the activity is adjusted to 28 U/ml F VIII:C, and the solution is packaged and freeze-dried.

EXAMPLE 2

Starting materials cryoprecipitate, 1 kg was dissolved at +37° C. in 3 l of dissolving buffer and then treated with 2×5% (v/v) Al(OH)$_3$ 4 l of solution were adsorbed at 25° C. for 15 minutes with 2×200 ml of 1% strength Al(OH)$_3$ in each case, and then centrifuged off at 3,000 rpm and stabilizers were added to the supernatant for the pasteurization.

Stabilizing and heating

For this purpose, the 4,040 ml of the Al(OH)$_3$ supernatant were made up to a final concentration corresponding to 100% (w/v) by the addition of 4,040 g of sucrose; subsequently, 545.4 g of glycine corresponding to 1.8 mol/l were added and the CaCl$_2$ concentration was adjusted to 5 mmol/l. The stabilized solution was adjusted to pH 7.3 with 2.5 N NaOH and was then heated at +60° C. for 10 hours. The F VIII:C activity was determined before and after heating and was 2.0 U/ml and 1.9 U/ml, respectively.

Preparing for the DEAE adsorption according to DE 3,432,083 the heated cryosolution (6,868 ml) was diluted 1:2 with 6,868 ml of dilution buffer and the pH was adjusted to 5.5 with 2N acetic acid.

Adsorption on DEAE-$^R$Sepharose CL-6B in batch process 13,736 ml of dilute cryosolution was adsorbed at room temperature for 4 hours with 300 ml of equilibrated DEAE-$^R$Sepharose CL-6B, and the Sepharose was then separated off.

Washing the $^R$Sepharose and transferring it into a column

The Sepharose loaded with F VIII was prewashed on a suction filter, then transferred into a column (diameter 7.2 cm) and treated with 3 l of washing buffer.

Elution of the DEAE-$^R$Sepharose column

The F VIII:C was displaced from the washed DEAE-$^R$Sepharose with an acetate-buffered and lysine-containing $CaCl_2$ solution (0.3 mol/l), and the eluate, 195 ml, was made up to a final concentration of 0.75% by the addition of 1.46 g of sucrose.

Dialysis 195 ml of eluate were dialyzed at +4° C. for 16 hours against 20 l of dialysis buffer. Of this material, the protein content was measured via the OD at 280 nm, the F VIII activity was determined and the yield and specific activity was calculated from the two values; in a stress test, portions were stored at 20° C., and the F VIII activity was determined after 24, 48 and 96 hours (see table, Experiment 2).

Adjusting the concentration and sterilization by filtration 218 ml of dialyzed F VIII:C were rendered sterile by filtration through Sartorius filters; the activity of the solution was adjusted to 28 U/ml was F VIII:C with dialysis buffer, and the solution was packaged and freeze-dried.

EXAMPLE 3

In analogy with Example 1, a solution of fresh cryoprecipitate was first adsorbed 1×5% (v/v) $Al(OH)_3$ and the supernatant after centrifugation was then adsorbed with a second amount of 5% (v/v) $Al(OH)_3$, 3% (w/v) moist ECTEOLA (120 g/4l) were added after 5 min at 25° C. and incubation took place for 15 min. Pasteurized, highly purified factor VIII was obtained as described above from the supernatant after separating off the adsorbent. As Experiment 3 demonstrates in the table, this method also leads to a stable product with good yield and high specific activity.

EXAMPLE 4

According to Example 1, 1 kg of cryoprecipitate was again freshly dissolved at 37° C. but then adsorbed only once with 5% (v/v) $Al(OH)_3$ 4 l of dissolved cryoprecipitate were adsorbed at +25° C. for 15 minutes with 200 ml of 1% strength $Al(OH)_3$ and the adsorbent was then centrifuged off at 3,000 rpm. Subsequently, so-called mixed absorption was carried out, with 1×5% (v/v) $Al(OH)_3$ adsorption and 3% QAE-$^R$Sephadex A50 initially 200 ml of 1% strength $Al(OH)_3$ were added to 4 l of the first $Al(OH)_3$ supernatant and the mixture was stirred for 5 min before 120 g of moist QAE-Sephadex A50 were added and adsorption at +25° C. was carried out for 15 minutes with it. The supernatant obtained after centrifugation was stabilized, pasteurized and purified via absorption on DEAE-$^R$Sepharose according to Example 1. Yield, specific activity and stability are indicated in the table (see Experiment 4).

EXAMPLE 5

As in Example 1, 1 kg of cryoprecipitate was dissolved with 3.0 l of buffer and adsorbed at 25° C. for 15 minutes with 200 ml of 1% strength $Al(OH)_3$ solution and the supernatant was obtained by centrifugation. Subsequently, it was treated as follows:

1× with 5% (v/v) $Al(OH)_3$, 3% (w/v) moist QAE-$^R$Sephadex A50 and 3% (w/v) moist ECTEOLA in each case; the adsorbents were added at 5 min intervals, incubated at 25° C. for 15 min and centrifuged off for 15 min after the addition of ECTEOLA (3,000 rpm). The pasteurization and final purification was also carried out according to Example 1. The final product is described with respect to yield and properties under Experiment 5 in the table.

EXAMPLE 6

According to Example 2, 1 kg of freshly dissolved cryoprecipitate was employed and adsorbed once with 5% (v/v) $Al(OH)_3$, and the supernatant was then adsorbed as follows;

1× with 5% (v/v) $Al(OH)_3$, then with 3% QAE, finally with 1% $Ca_3(PO_4)_2$:

Initially 4 l of the first $Al(OH)_3$ supernatant were treated with a further 200 ml of 1% strength $Al(OH)_3$ (5 min, 25° C.), then with 120 g of QAE-$^R$Sephadex A50 under identical conditions and finally with 40 g of $Ca_3(PO_4)_2$ at +25° C. for 15 min. All adsorbents were centrifuged off together and stabilizers were added to the supernatant after centrifugation, and it was pasteurized, diluted and the F VIII purified on DEAE-Sepharose according to Example 1. The eluate had an impressively high specific activity (see Experiment 6 in the table).

Those cryoprecipitates which are processed according to EP 0,018,561 B1 or EP 0,032,655 to give F VIII concentrates also lead to stable and highly active products with a good yield when the starting material was treated by adsorption according to the invention. This is shown in the following example.

EXAMPLE 7

6 kg of crude cryoprecipitate are dissolved at 37° C. with 18 l of a buffer of the following composition: 0.08 mol/l NaCl, 0.27 mol/l glycine, 0.5 U/ml heparin, 0.1 U/ml AT III, pH 6.0. 24 l of crude cryosolution were obtained and were initially absorbed with 1×5% (v/v) $Al(OH)_3$ For this 1.2 l of 1% strength $Al(OH)_3$ were added to 24 l of crude cryosolution at 25° C., were stirred for 15 min and the adsorbent was centrifuged off at 3,000 rpm; subsequently a mixed adsorption was carried out with 5% (v/v) Al(OH)$_3$ and 3% QAE-$^R$Sephadex A50

1.2 l of 1% strength Al(OH)$_3$ were once again added to 24 l of the first Al(OH)$_3$ supernatant and stirred for 5 min; subsequently, the solution was adsorbed at 25° C. for a further 15 min with 720 g of moist QAE-$^R$Sephadex A50. The supernatant obtained by centrifugation was worked up according to Ma 339 (EP 0,018,561; U.S. Pat. No. 4,297,344) to give F VIII concentrate and freeze-dried.

The reconstituted final product showed impressively good stability when left standing at room temperature:

| F VIII:C | activity after reconstitution: | 29 IU/ml |
|---|---|---|
| | after 2 hours at 23° C. in solution | 27 IU/ml |
| | after 6 hours at 23° C. in solution | 29 IU/ml |
| | after 24 hours at 23° C. in solution | 30 IU/ml. |

The buffers used in the examples are:

| Dissolving buffer: | 0.08 mol/l NaCl |
|---|---|
| | 0.27 mol/l glycine |
| | +0.1 U/ml AT III |
| | +0.5 U/ml heparin |
| Dilution buffer: | 0.2 mol/l lysine |
| | 0.2 mol/l Na acetate |
| | pH 5.5 |
| Washing buffer: | 0.1 mol/l lysine |
| | 0.1 mol/l Na acetate |
| | 0.017 mol/l NaCl |
| | 0.0125 mol/l CaCl$_2$ |
| | pH 5.5 |
| Elution buffer: | 0.1 mol/l lysine |
| | 0.1 mol/l Na acetate |
| | 0.3 mol/l CaCl$_2$ |
| | pH 5.5 |
| Dialysis and packaging buffer: | 0.15 mol/l NaCl |
| | 0.75% sucrose |
| | 3% glycine |
| | pH 6.9 |

We claim:

1. A process for the preparation of factor VIII, which comprises the steps of:
   (a) pretreating the factor VIII-containing solution by adsorbing said solution with at least an Al(OH)$_3$ adsorbent and a basic anion exchanger adsorbent, under conditions such that the adsorbents bind enzymes and proenzymes which have amidolytic/proteolytic activity and degrade factor VIII; and
   (b) recovering said factor VIII from said solution which has been pretreated.

2. The process as claimed in claim 1, wherein the pretreatment is carried out with a basic anion exchanger having a hydrophilic matrix and anionic groups.

3. The process as claimed in claim 1, wherein the pretreatment is carried out with a basic anion exchanger having a matrix based on polysaccharides and anionic groups.

4. The process as claimed in claim 1, wherein the pretreatment is carried out at a pH of 6.5–7.5 and a conductivity of 10–15 mS.

5. The process as claimed in claim 1, wherein the pretreatment is carried out in a medium which does not contain any citrate ions.

6. The process as claimed in claim 1, wherein the adsorbents are added sequentially and the supernatant is then separated off.

7. The process as claimed in claim 1, wherein pasteurization is additionally carried out.

8. The process as claimed in claim 1, wherein the adsorbents are used in an amount of about 20–30 g/l of solution.

9. The process of claim 1 wherein said factor VIII-containing solution is subjected to two adsorptions on Al(OH)$_3$ and at least one adsorption on a basic anion exchanger.

10. The process as claimed in claim 1, wherein said solution containing factor VIII is selected from the group consisting of a factor VIII-containing plasma fraction, a dissolved cryoprecipitate and a Cohn fraction I.

11. The process as claimed in claim 1 wherein the factor VIII-containing solution is pretreated two times with Al(OH)$_3$, one time with QAE-Sephadex and one time with ECTEOLA.

12. The process as claimed in claim 1, wherein the factor VIII-containing solution is pretreated two ties with Al(OH)$_3$ and one time with QAE-Sephadex.

13. The process as claimed in claim 1, wherein the factor VIII-containing solution is pretreated two times with Al(OH)$_3$ and one time with ECTEOLA.

14. A process for the preparation of factor VIII, which comprises the steps of:
   (a) subjecting a factor VIII-containing plasma fraction to an adsorption on Al(OH)$_3$ and an adsorption on an anion exchanger under conditions such that the adsorbents bind enzymes and proenzymes which have amidolytic/proteolytic activity and degrade factor VIII; and
   (b) obtaining the factor VIII from said plasma fraction.

15. A process for the preparation of factor VIII, which comprises the steps of:
   (a) pretreating a factor VIII-containing solution by adsorbing said solution with a mixture of at least Al(OH)$_3$ and a basic anion exchanger under conditions such that the adsorbents bind enzymes and proenzymes which have amidolytic/proteolytic activity and degrade factor VIII; and
   (b) recovering said factor VIII from said solution which has been pretreated.

16. A process for the preparation of factor VIII, which comprises the steps of:
   (a) pretreating a factor VIII-containing solution by adsorbing said solution with at least one adsorbent selected from the group consisting of Al(OH)$_3$ and a basic anion exchanger under conditions such that the adsorbents bind enzymes and proenzymes which have amidolytic/proteolytic activity and degrade factor VIII;
   (b) separating the adsorbent from the factor VIII-containing solution;
   (c) treating the factor VIII-containing solution obtained from (b) by adsorbing said solution with at least one adsorbent selected from the group consisting of Al(OH)$_3$ and a basic anion exchanger but with a different adsorbent than that used previously, under conditions such that the adsorbents bind enzymes and proenzymes which have amidolytic/proteolytic activity and degrade factor VIII;
   (d) separating and recovering factor VIII from said solution which has been treated.

* * * * *